(12) United States Patent
Pieczarek et al.

(10) Patent No.: US 9,902,930 B2
(45) Date of Patent: Feb. 27, 2018

(54) LABORATORY INCUBATOR HAVING IMPROVED MOISTURE DISTRIBUTION

(71) Applicant: Thermo Electron LED GmbH, Langenselbold (DE)

(72) Inventors: Waldemar Pieczarek, Langenselbold (DE); Juergen Andreas Schneider, Rodenbach (DE); Hermann Stahl, Bruchmuehlen (DE)

(73) Assignee: Thermo Electron LED GmbH, Langenselbold (DE)

( * ) Notice: Subject to any disclaimer, the term of this patent is extended or adjusted under 35 U.S.C. 154(b) by 75 days.

(21) Appl. No.: 14/454,419

(22) Filed: Aug. 7, 2014

(65) Prior Publication Data

US 2015/0050725 A1    Feb. 19, 2015

(30) Foreign Application Priority Data

Aug. 16, 2013    (DE) .................. 10 2013 013 665

(51) Int. Cl.
*C12M 1/00*    (2006.01)
*C12M 3/00*    (2006.01)
(Continued)

(52) U.S. Cl.
CPC ............. *C12M 41/14* (2013.01); *B01L 1/025* (2013.01); *C12M 23/34* (2013.01); *C12M 29/26* (2013.01);
(Continued)

(58) Field of Classification Search
CPC ...... C12M 41/14; C12M 41/12; C12M 41/18; C12M 41/20; B01L 7/00
See application file for complete search history.

(56) References Cited

U.S. PATENT DOCUMENTS 3,929,584 A    12/1975 Mansfield
4,689,303 A *    8/1987 Kraft .................. B01L 7/00
                                         126/21 A
(Continued)

FOREIGN PATENT DOCUMENTS

DE                659150 A    4/1938
DE        102004049210 A1    6/2005
(Continued)

OTHER PUBLICATIONS

Georg Hasse, English Translation of Claims for German Application No. DE659150A, published Apr. 27, 1938 (1 page).
(Continued)

*Primary Examiner* — Nathan A Bowers
(74) *Attorney, Agent, or Firm* — Wood Herron & Evans LLP (57) ABSTRACT

The present invention relates to a laboratory incubator, more particularly, a gassing incubator, comprising an outer housing incorporating a door and an inner housing surrounding an internal chamber, which comprises a floor, a ceiling, three side walls and a lateral surface that is capable of being closed by said door or by an additional, inner door, and in which a flow channel is present, which comprises at least one air inlet opening in an end region and at least one air outlet opening in a different end region, wherein said at least one air outlet opening is formed such that effluent air is guided along at least one of the side walls and/or the lateral surface in the peripheral region of the internal chamber, and wherein a water reservoir capable of being heated is disposed within the flow channel such that air flowing in the flow channel is passed across or through said water reservoir.

26 Claims, 4 Drawing Sheets

(51) Int. Cl.
 *B01L 1/02* (2006.01)
 *C12M 1/12* (2006.01)
(52) U.S. Cl.
 CPC ........ *C12M 37/02* (2013.01); *B01L 2200/146* (2013.01); *B01L 2200/147* (2013.01); *B01L 2300/043* (2013.01); *B01L 2300/0829* (2013.01); *B01L 2300/10* (2013.01)

(56) References Cited

U.S. PATENT DOCUMENTS

| | | | | |
|---|---|---|---|---|
| 4,701,415 | A * | 10/1987 | Dutton | B01L 1/00 435/286.6 |
| 4,892,830 | A * | 1/1990 | Findley | B01L 1/00 236/3 |
| 5,730,355 | A * | 3/1998 | Lessard | A61G 11/00 237/14 |
| 5,976,871 | A * | 11/1999 | Walker | B01L 1/04 312/1 |
| 6,255,103 | B1 * | 7/2001 | Tamaoki | C12M 41/14 219/407 |
| 6,333,004 | B1 | 12/2001 | Sheldon | |
| 6,503,751 | B2 * | 1/2003 | Hugh | C12M 23/48 219/400 |
| 6,878,177 | B2 | 4/2005 | Lohr et al. | |
| 7,838,286 | B2 * | 11/2010 | Tamaoki | C12M 41/14 435/303.1 |
| 2005/0084420 | A1 | 4/2005 | Osawa et al. | |
| 2006/0057713 | A1 * | 3/2006 | Cecchi | C12M 23/48 435/303.1 |
| 2008/0113599 | A1 * | 5/2008 | Ross | B01L 1/04 454/61 |
| 2010/0062522 | A1 * | 3/2010 | Fanning | C12M 41/14 435/303.1 |
| 2011/0107788 | A1 | 5/2011 | Stahl et al. | |

FOREIGN PATENT DOCUMENTS

| | | |
|---|---|---|
| EP | 1552888 A2 | 7/2005 |
| JP | 07-227270 A | 8/1995 |

OTHER PUBLICATIONS

Sanyo Electric Co. Ltd., English Translation of Abstract for JPH07227270A, published Aug. 29, 1995 (1 page).
Espacenet, English Machine Translation of German Application No. DE102004049210A1, published Jun. 2, 2005, retrieved from http://worldwide.espacenetcom on Jul. 28, 2014 (9 pages).
Espacenet, English Machine Translation of European Application No. EP1552888A2, published Jul. 13, 2005, retrieved from http://worldwide.espacenet.com on Jul. 28, 2014 (14 pages).

* cited by examiner

LABORATORY INCUBATOR HAVING IMPROVED MOISTURE DISTRIBUTION

CROSS-REFERENCE TO RELATED APPLICATION

The present application claims priority under 35 U.S.C. § 119 of German Patent Application No. 10 2013 013 665.2, filed Aug. 16, 2013, the disclosure of which is hereby incorporated herein by reference in its entirety.

FIELD OF THE INVENTION

The present invention relates to a laboratory incubator, more particularly a gassing incubator, comprising an outer housing and an inner housing delimiting an internal chamber used for the storage of samples. The internal chamber can be accessed via a door in the outer housing. If necessary, the inner housing may comprise an additional, inner door situated adjacent to the outer door and separately closing the internal chamber. Such an inner door can, for example, be made of glass (see, U.S. Pat. No. 6,878,177 B2).

BACKGROUND OF THE INVENTION

Laboratory incubators usually serve to store samples, more particularly, biological and/or microbiological samples, in the internal chamber thereof, under predefined conditions such as specific temperature and humidity conditions and, in the case of gassing incubators, a defined gas atmosphere. In such situations, the attempt is usually made to imitate the conditions of the human or animal body. Frequently, selected conditions are therefore a temperature of approximately 37° C. and an optimally high humidity level of generally at least 60%, preferably, at least 80% and, more preferably, at least 90%, without, however, allowing condensation of moisture to take place on the walls or other regions of the incubator. Such regions of moisture present potential contamination centers.

A number of options are known in the prior art for the creation of a humid atmosphere in the internal chamber of a laboratory incubator. A first such option is the provision of a water reservoir inside the incubator, from which reservoir water is vaporized by means of heating (see, EP 1552888 A2). This option, however, presents a major problem in the form of the ease of contamination of the water bath and the risk of contamination of the samples stored in the incubator.

For the purpose of ensuring an even distribution of temperature and moisture content in the internal chamber, the air in the internal chamber is usually circulated by means of a fan. This often involves conducting the air evenly across the entire internal chamber upwardly from the floor toward the ceiling with the air being conducted across the water bath mounted on the floor, where it absorbs moisture and conveys the same into the internal chamber. A fan is disposed at the ceiling and is adapted to suck in the air and conduct it through a duct located between the outer and inner housings, thus, causing it to flow back toward the floor along the ceiling and side wall (see, U.S. Pat. No. 6,878,177 B2 and U.S. Pat. No. 6,333,004 B1). However, such ventilation in the internal chamber bears the risk of the samples stored therein becoming desiccated or contaminated by germs entrained from the water bath. Furthermore, an issue occurs when starting up the incubator or after opening the door and, thus, disturbing the atmosphere of the internal chamber in that a relatively long period of time before the levels of moisture content and temperature in the internal chamber reach or return to the desired level.

There has thus been a certain demand for a laboratory incubator that allows for the storage of samples in its internal chamber at a highly constant level of moisture content and with the least possible risk of contamination or desiccation. It is an object of the present invention to provide such a laboratory incubator.

SUMMARY OF THE INVENTION

In its broadest aspect, the present invention, therefore, relates to a laboratory incubator, preferably a gassing incubator, comprising an outer housing containing a door and an internal chamber enclosed by an inner housing comprising a floor, a ceiling, three side walls, and a lateral surface, closable by means of the door or an additional, inner door and comprising a duct with at least one air inlet opening in an end region and at least one air outlet opening in another end region, wherein the at least one air outlet opening is designed such that exiting air is conducted along the edge of the internal chamber and at least one of the side walls and/or the lateral surface, a heatable water reservoir being disposed inside the duct in such a manner that air flowing through the duct flows across or through the water reservoir.

The improved characteristics of the laboratory incubator according to the present invention are achieved, on the one hand, by means of a specific flow control within the internal chamber, and, on the other hand, by the fact that the reservoir is disposed within the duct in such a way that the air passing through the laboratory incubator flows either across or through the water reservoir. The placement of the water reservoir in the duct means that it is spatially separated from the internal chamber and the samples stored therein. In comparison with the water troughs conventionally mounted in open configuration on the floor of the internal chamber, this has the advantage, on the one hand, that contamination of the water reservoir can be reduced and, on the other hand, that fewer germs will be entrained from the water by the air circulating through the internal chamber, with a lower risk of pollution of the samples.

The air circulation inside the laboratory incubator, referred to below simply as an incubator, is likewise guided in such a way that the air flowing inside the duct between the at least one air inlet opening and the at least one air outlet opening is kept spatially separated from the internal chamber. In that respect, a duct within the scope of the present invention means an enclosed space with provision for air to enter via the at least one air inlet opening and for said air to leave only through the at least one air outlet opening in a different end region of the duct. This does not, of course, exclude the possibility of other inlet or outlet orifices being present in the section of the duct between the said air inlet opening and said air outlet opening. However, the air flowing in the duct during normal operation of the incubator cannot flow through said orifices. For example, they may be openings in the duct through which additional gases, for example, nitrogen or carbon dioxide, can flow into the duct. Likewise, conceivable are supply lines for disinfectants or similar agents, optionally in combination with a drain hole closed, for example, by means of a valve and by way of which fluids, for example, a cleaning agent, can be discharged from the duct during a cleaning phase.

As mentioned above, during normal operation of the incubator during which samples are stored under specific conditions in the internal chamber, air flows through the duct exclusively in such manner that it enters via the at least one air inlet opening in an end region of the duct, flows through the duct, and exits solely via the at least one air outlet opening in a different end region of the duct. This is achieved by the expelled air entering the internal chamber in its peripheral region in such manner that the air flows along at least one of the side walls and/or the open lateral surface that allows access to the internal chamber. This does not necessarily mean that the air must be blown directly onto a side wall or the lateral surface. It does, however, mean that it is possible for the air to flow first for some distance along the ceiling or the floor, with the result that it is only redirected once it comes into contact with the nearest side wall or lateral surface, along which it then continues to flow. It is essential that the air flows into the internal chamber only in its peripheral region having a width of, for example, not more than 20%, preferably, not more than 15%, of the width of the internal chamber between the side wall or lateral surface along which the air is flowing, and the side wall or lateral surface opposite thereto. For the purpose of limiting the air supply from the air outlet opening to the peripheral region, the air flow is appropriately controlled so as to take place parallel to, or substantially parallel to, the side wall or lateral surface along which air is conducted. In this case, "substantially parallel" means that the angle at which the air flow is conducted in relation to the side wall or lateral surface is not more than 5° and in particular not more than 2°. The effluent air is, therefore, not conducted according to the usual practice, in other words, across the entire internal chamber and, thus, also across the sample storage area, but exclusively in the immediate vicinity of the inner housing so that the interior of the internal chamber and the samples stored therein are not directly influenced by the effluent air. Such a procedure significantly reduces the risk of desiccation of the samples.

The flow control of the air leaving the at least one air outlet opening is preferably carried out such that a substantially laminar flow is generated which shows a minimum degree of turbulence. The air outlet opening can, for example, be in the form of a slot nozzle adapted to cause the effluent air to take the shape of an air curtain flowing along the inner housing. The air exchange with the central region of the internal chamber does, therefore, not take place due to the effluent air being directly conducted to the center of the internal chamber but due to the low degree of turbulence generated at the edge of the air curtain in the direction of the center of the internal chamber. At this point, however, the air flows at a significantly slower rate than in the main laminar flow itself. The samples situated in the internal chamber are therefore only slightly affected by the air subjected to such low rates of flow and there is a significantly lower risk of them becoming desiccated than would be the case if they were subjected to a direct air flow.

The flow control is preferably carried out with the at least one air outlet opening situated in a peripheral region of the ceiling, in other words, with the air flowing downwardly in the internal chamber. Alternatively, or additionally, the air outlet opening may be disposed in an upper peripheral region of at least one side wall, adjacent to the ceiling. For the purpose of achieving a maximumly vertical air flow extending from the ceiling toward the floor of the inner housing, the at least one air inlet opening sucking air into the duct is preferably disposed in an outer peripheral region of the floor, in other words, appropriately below the at least one air outlet opening. It is, however, basically possible to reverse the direction of air flow, in other words, to reverse the arrangement of the air inlet and outlet openings such that air is conducted upwardly from the floor toward the ceiling.

In any of the above situations, it is basically possible to guide the air along one side wall only or along the open lateral surface only, or along a number of side walls or along one side wall or a number of side walls and the open lateral surface.

In one embodiment, air flows exclusively along the open lateral surface of the inner container of the incubator, said lateral surface being closable by means of a door and optionally by an additional, inner door. Here again, the air is preferably conducted downwardly so that the air outlet opening is situated in a region above the door or inner door and the at least one air inlet opening is disposed in a region adjacent to the lower edge of the door or inner door. When controlled in this manner, the moist air initially makes contact with the upper region of the door which is slightly warmer than the section of door near the floor. Unwanted condensation on the door is, thus, particularly well avoided. Here again, however, reverse flow control in an upward direction is basically conceivable.

A further advantage of guiding the air flow exclusively along the outer peripheral region of the internal chamber, as opposed to along its center, lies in the fact that the air flows along surfaces that are usually heated during operation of the incubator. Incubators usually comprise wall heaters for the heating of the walls of the inner container of the internal chamber. It is also customary to heat the door as well. The application and, thus, of heat to the surfaces along which the air circulating in the internal chamber flows reduces the risk of the entrained moisture condensing out of the air onto these surfaces. This, however, results in a reduced risk of contamination of the internal chamber due to a drastic reduction of the risk of moist spots developing, as compared with conventional incubators.

For reasons of space, the duct through which the air flows spatially separated from the internal chamber is suitably situated outside the internal chamber and, more particularly, in the space between the inner and outer housings of the incubator. In this respect, an arrangement is preferred in which the air flow is conducted in a barrel-like manner around the internal chamber with the duct extending externally along the floor, one lateral surface, and the ceiling of the inner housing. The water reservoir present inside the duct can be basically positioned at any preferred point in the duct. It is, however, advantageous to position the water reservoir below the floor of the inner housing. The water reservoir may be in the form of a closed container, except for the inlet and outlet pipes. When the air is passed through the water present in the water reservoir, a blocking means, for example, a diaphragm permeable to air but impermeable to water, a check valve, or the like, is located at the inlet to prevent water from leaking away from the reservoir. It is preferable for the water reservoir to be basically of a type similar to the water troughs used in the internal chamber of prior art incubators. In this situation, however, according to the present invention, it is not disposed as an open trough in the internal chamber but inside the duct, spatially separated from the internal chamber. The water in the water reservoir is heated in the usual way according to the prior art, for example, by means of heating elements disposed below the floor of the water trough or in a similar manner. The water vapor thus developed is absorbed by the air flowing through the duct and across or through the water reservoir, the air accumulates moisture and conveys this through the duct toward the at least one air outlet opening and, thence, into the internal chamber.

For the purpose of maintaining the desired water temperature, the water reservoir is equipped with a temperature sensor transferring measurement results in a manner known per se to an evaluation and control unit utilized for the control of the water reservoir heating device. It is, particularly, appropriate to arrange the temperature sensor at a point of the water reservoir that corresponds with the level of the minimum desired water level. In the event of the water level falling below the minimum water level, the measurement results obtained via the temperature sensor change drastically. Such sudden change can serve as an indicator for the need to raise the water level in the water reservoir. The evaluation and control unit can issue an appropriate warning to the operator or make provision for automatic replenishment of the water in the water reservoir. Due to the temperature measurement results, the subsequently necessary resetting of the water temperature affecting the levels of temperature and moisture content in the internal chamber can be achieved quicker and more accurately than was previously possible, when reheating of the water reservoir was effected only due to changes in temperature and/or moisture content in the internal chamber.

It is a known standard practice in the prior art to regulate the temperature of the internal chamber of the incubator jointly with the temperature of the water bath. This is, also, possible within the scope of the present invention. Separate controlling of the heating device for the internal chamber and the heating device for the water reservoir is, however, preferred. The temperature control according to the measurement results of the separate temperature sensors for the internal chamber and the water reservoir has the advantage that it enables significantly more accurate temperature adjustment while at the same time providing improved recovery time after system disturbances. Such a disturbance can be caused, for example, by changes in the outer temperature or by opening the door to the internal chamber. For the purpose of counteracting the loss of moisture content and temperature caused in such a way that is harmful to samples, it is advisable to increase the output of the heating device for the water bath and to adjust the heating ratio between the inner wall heater and the water reservoir heater in favor of the latter. This is, of course, not possible if both heating devices are coupled. After the door is closed, however, the heating output for the water reservoir must not remain at an increased level for too long a period of time as this results in unintentionally high entrainment of moisture into the internal chamber and, thus, possibly in condensation of moisture. Such specific control is also significantly easier to achieve in the device according to the present invention as the decoupling of the internal chamber heater from the water reservoir heater allows a significantly more precise and time-reduced setting of the desired temperature and humidity levels.

The design of the cold spot according to the present invention provides for even more accurate control of moisture levels within the interior chamber. A cold point, also referred to as a "cold spot", is a region of reduced temperature in relation to the temperature of the interior, and is used for the removal of excess moisture from the interior by condensation. In the incubators of the prior art, such a cold spot is usually situated within the interior itself and forms part of the interior wall, in which the temperature is reduced by attaching a thermal bridge to the outside in relation to the surrounding parts of the housing. Such a cold spot is usually situated at a lower region of the side wall of the inner housing. Excess moisture present in the interior condenses out at this point. There is, thus, always a spot of moisture present in the interior, representing a source of undesirable contamination. According to the present invention, the cold spot is now relocated from inside the internal chamber to the flow channel in the direction of flow to beyond the water reservoir. This cold spot serves the same purpose as in the prior art, in other words, the condensation of excess moisture. Due to the spatial separation of the water reservoir and the cold spot situated downstream thereof, the risk of contamination in the interior chamber is, however, significantly reduced compared with the solutions provided in the prior art.

The cold spot can principally be of the same design as in the prior art. Passive or active cooling of such a cold spot is possible. In the most basic variant, it may, for example, be sufficient to move the cold spot to a position, or to create heat-conducting contact thereof with a position, which is set at a sufficiently low temperature. In addition, a temperature controlling device may be provided to facilitate adjustment of the temperature of the cold spot. Such a device may, for example, consist of a temperature bridge in heat-conducting contact with the outer housing. This is usually, for example, a metal strip or, more particularly, an aluminum strip. Alternatively, a hollow member filled with a cooling fluid can be used to facilitate cooling. In particular, this can consist of a pipe for conduction of water or a similar cooling fluid. In a preferred variant, such cooling fluid can be drained from the hollow member. This has the particular advantage of making it possible to virtually switch off the cold spot by draining away the cooling fluid. When there is no cooling fluid present in the hollow member to conduct heat, no further cooling of the cold spot takes place and its temperature becomes substantially equal to the temperature of the environment. This may be of use if, for example, the overall temperature in the internal chamber is to be raised during a disinfection process taking place at a high temperature. A heat-dissipating thermal bridge from inside the internal chamber would be contra-productive in this situation and would delay heating of the internal chamber. On completion of such a disinfection process, the hollow member can be replenished with cooling fluid to resume its function as a thermal bridge. Such replenishing can take place either by hand or automatically, for example, by means of a suitable pump connected to a cooling fluid reservoir.

In a further embodiment, the cold spot temperature control can be effected actively, for example, by means of a temperature control device in the form of a fan or an electrical cooling and/or heating device. The latter enables rapid heating of the cold spot in specific applications, for example, when condensation of moisture is to be avoided. Such a situation can be a disinfection process as mentioned above or a disturbance wherein an unwanted fall in moisture content must be balanced out as rapidly as possible.

For the purpose of achieving specific temperature control of the cold spot, a temperature sensor is preferably disposed near the cold spot. By means of the measurement results obtained from such a sensor, the temperature control device can be controlled according to the required cold spot temperature. In such a situation, it is possible to specifically preset the cold spot temperature according to the conditions desired in the internal chamber. A higher default temperature for the cold spot results in higher moisture levels in the internal chamber. This may, for example, be advisable if microtiter plates are to be stored in the internal chamber. Such plates present a very low volume per sample, thereby increasing the risk of desiccation. Conversely, it may be advisable to keep moisture levels in the internal chamber relatively low in the case of samples having high fluid contents and high condensation rates, to prevent an unwanted condensation of moisture from occurring in the internal chamber. In such situations, a low temperature setting for the cold spot can be predefined. In such a situation, it is principally possible to predefine the parameter "cold spot temperature" to a specific value from the outset. This may, also, be carried out in advance after consultation with the incubator operator and depending on the intended use. Alternatively, the operator may be provided with a number of options for such a parameter for selection during each operation. The parameter "water reservoir temperature" can also similarly be predefined to a suitable value, or a number of different parameters can be for selection during operation.

The option of specific temperature control of the cold spot simultaneously in conjunction with specific temperature control of the water reservoir makes it possible to carry out specific adjustments of moisture levels in the internal chamber that have not been possible yet. Not only can the desired moisture levels be maintained in a very precise manner, but it is, also, possible to return them very rapidly to the desired values and to respond to any detected variations in the minimum amount of time. The aforementioned very rapid resetting of the moisture values in the internal chamber following disruption caused, for example, by opening the door can be further improved on due to the independent temperature control of the cold spot. If a reduction of moisture levels in the internal chamber is caused due to the door being opened, it is possible, for example, to increase the cold spot temperature and, thus, prevent the condensation of water vapor on the cold spot. Due to the simultaneous raising of the water reservoir temperature as described above, a large volume of moisture is conveyed very rapidly into the internal chamber to facilitate quick recovery of the moisture levels. On the other hand, by extracting excess moisture from the moisture-rich air flow directly at the cooled cold spot, after closing the door, a lowering of the cold spot temperature can prevent unwanted leakage of moisture from the very warm water reservoir into the internal chamber, where it consequently condenses. The occurrence of excess moisture levels in the internal chamber can, thus, be prevented in a particularly efficient manner.

As described above, with regard to the water reservoir heating device, it is also preferred in the case of the cold spot temperature control device to regulate this in dependence on measurement results relating to specific operating parameters of the incubator. In particular, when regulating the cold spot temperature control device and/or the water reservoir heating device, measurement results obtained from at least one of the following sensors are considered: a sensor for ascertaining the temperature in the internal chamber, a sensor for ascertaining moisture levels in the internal chamber, a sensor for ascertaining whether the door is open or closed, and a sensor for ascertaining whether the inner door is open or closed.

The combined control of the heating device for the water reservoir and the temperature control device for the cold spot make it possible, in particular, to manipulate the moisture values in the internal chamber very specifically and rapidly so as to comply with the desired moisture values. Due to the separation of the water reservoir and the cold spot, it is now possible to predefine larger differences in temperature between these entities than was previously possible in the prior art. Where maximum temperature differences of 1° C. have been customary, it is now possible to differentiate between temperatures lying up to 3° C. apart. This significantly broadens the control range for temperatures and moisture levels in the internal chamber. It is, furthermore, possible to shorten the start-up phase following the restart or initial start of the incubator as opposed to the conventional start-up phases via the separate setting and controlling of the water reservoir temperature and the cold spot temperature. The start-up phase is usually considered to be complete when the moisture levels in the internal chamber remain constant over a predefined, relatively long period of time. Moisture level measurement usually occurs by means of zero adjustment of a heat conductivity measuring cell. In the case of the incubator according to the present invention, further values, in other words, the water bath temperature and the cold spot temperature, are available, so that the start-up phase may be considered to be complete as soon as the water bath temperature and the cold spot temperature have reached a desired value. Such setpoint values are reached particularly quickly when the water bath temperature can be set and monitored independently of the temperature of the internal chamber. Not even the process of exceeding the water reservoir temperature, for example, during a rapid heating operation, will usually result in an unwanted rise in the moisture level in the internal chamber due to excess moisture condensing from the air before reaching the internal chamber by way of the specific regulation of the cold spot. In a more basic variant, instead of separate temperature control of the water reservoir and the cold spot, an incubator without such control is feasible in which the heating ratio of the water reservoir and the cold spot is predefined at a constant value. In such a situation, a number of the advantages described above may however be achieved either not at all or only to a limited extent.

The precise adjustability of moisture levels in the internal chamber of the incubator according to one embodiment of the present invention prevents the moisture contained therein from condensing and forming a source of contamination. The water reservoir represents a further source of contamination. The risk of germs traveling from the water bath into the internal chamber and polluting the samples contained therein is already significantly reduced in the incubator according to the present invention by the water reservoir being arranged inside the flow channel and not immediately in the internal chamber but spatially separated therefrom. In addition, the arrangement of the water bath in the flow channel provides the facility to dispose a filter in front of and/or behind the water reservoir. Such filter disposed in front of the water reservoir in the direction of flow, prevents germs or other pollutants from being entrained into the water reservoir, thus, lengthening the intervals at which an exchange of water becomes necessary. A filter disposed behind the water reservoir in the direction of flow prevents germs or other pollutants present in the water from being conveyed by the air flowing through or across the water reservoir downstream in the direction of the at least one air outlet opening and thence into the internal chamber. If conventional HEPA or ULPA filters are used, as is fundamentally already the case in incubators, germs usually occurring inside incubators can be withheld. Less effective filters are, however, also usable, for example, in the form of membranes or other commonly used filter materials that may not guarantee sterility but do, however, retain other pollutants. Such less effective filters can be used, for example, at the water reservoir inlet. At the water reservoir outlet facing towards the internal chamber of the incubator, however, it is preferred to use HEPA or ULPA filters to prevent germs from entering the internal chamber.

A fan is appropriately utilized to cause movement of the air within the flow channel and in the internal chamber of the incubator in the manner fundamentally previously known for laboratory incubators. Such a fan can, for example, be a radial fan. Such a fan is also suitably disposed within the flow channel. It can fundamentally be mounted at any suitable location, preferably, downstream of the water reservoir and, more particularly, beyond the cold spot. To prevent pollution caused by the fan from being conveyed into the internal chamber, a filter, for example, again an air-permeable membrane, a HEPA or a ULPA filter, can be disposed downstream of the fan inside the flow channel, in particular, adjacent to the at least one air outlet opening. As excess pressure occurs in the flow channel between the fan and the filter, it is advisable for the channel to be sealed off in this region to such an extent that air cannot escape from the flow channel by passing the filter.

It is particularly appropriate to operate the fan in such a manner that a constant speed of flow prevails in the internal chamber and in the flow channel. If filters are mounted within the flow channel, the resistance to flow gradually rises with increasing allocation. For the purpose of securing a constant volumetric flow, it is, therefore, necessary to adjust the fan output accordingly, in particular, to boost it when the filters gradually become choked. This can be achieved by allocating a flow resistance meter to a filter in the flow channel and by controlling the fan output according to the measurement results obtained from such a flow resistance meter. If system disruption occurs, for example, by opening the door(s) to the internal chamber, it may be advisable to adjust the fan output. If moisture levels fall due to the door being opened, a more rapid reinstatement of the desired moisture levels may be achieved, for example, by increasing the fan output following closure of the door(s) for the purpose of increasing the intake of moisture into the internal chamber. Once the setpoint value has been reached, the fan output may be returned to the normal, lower flow rate. Furthermore, brief periods of increased fan output may be useful in the event of pollution entering the incubator, necessitating removal thereof from the system as quickly as possible via a HEPA or ULPA filter. A fan output different from the output required during normal sample storage operation may also be selected for other operational steps, for example, during a disinfecting procedure or when starting or restarting the incubator. For example, more rapid setting of the atmosphere of the internal chamber by means of increased fan output reduces the response time of the sensors and, thus, reduces the system down-time. Furthermore, sensors can be disposed at larger distances from each other, since it is possible to set like conditions more rapidly at positions set further apart. Furthermore, and for the same reason, gas inlets and corresponding gas sensors can be set at positions further apart. Conversely, in the event of a gas inlet and the corresponding sensor being set too close to each other, the fan output can be lowered to increase the system down-time. This procedure may be transferred to other sensors and measuring parameters.

Not only air, but also other gas atmospheres can be transported in the flow channel and in the internal chamber of the incubator. It is usual, for example, in so-called gassing incubators to enrich the atmosphere with carbon dioxide to achieve an acidic pH-value. This is also possible in the laboratory incubator according to the present invention. In fact, there is the particular advantage over incubators of the prior art in which it is frequently observed that moisture levels fall in an undesirable manner by adding further gases to the air. According to the present invention, this can be prevented by conducting a gas, for example, nitrogen or carbon dioxide, into the flow channel, appropriately at a point upstream of the water reservoir. As a result, before the gas enters the internal chamber of the incubator, it flows across or through the water bath, where it accumulates moisture, and is then conducted into the internal chamber with the desired moisture content, together with the air flowing in the flow channel. In this way, samples are successfully prevented from desiccation.

BRIEF DESCRIPTION OF THE DRAWINGS

The present invention is described below in greater detail with reference to drawings. These drawings are purely diagrammatical and merely serve to describe preferred embodiments of the present invention without restricting the present invention to the embodiments described. Like components are identified in the drawings by like reference numerals. In the drawings.

DETAILED DESCRIPTION OF THE INVENTION

Figure 1:
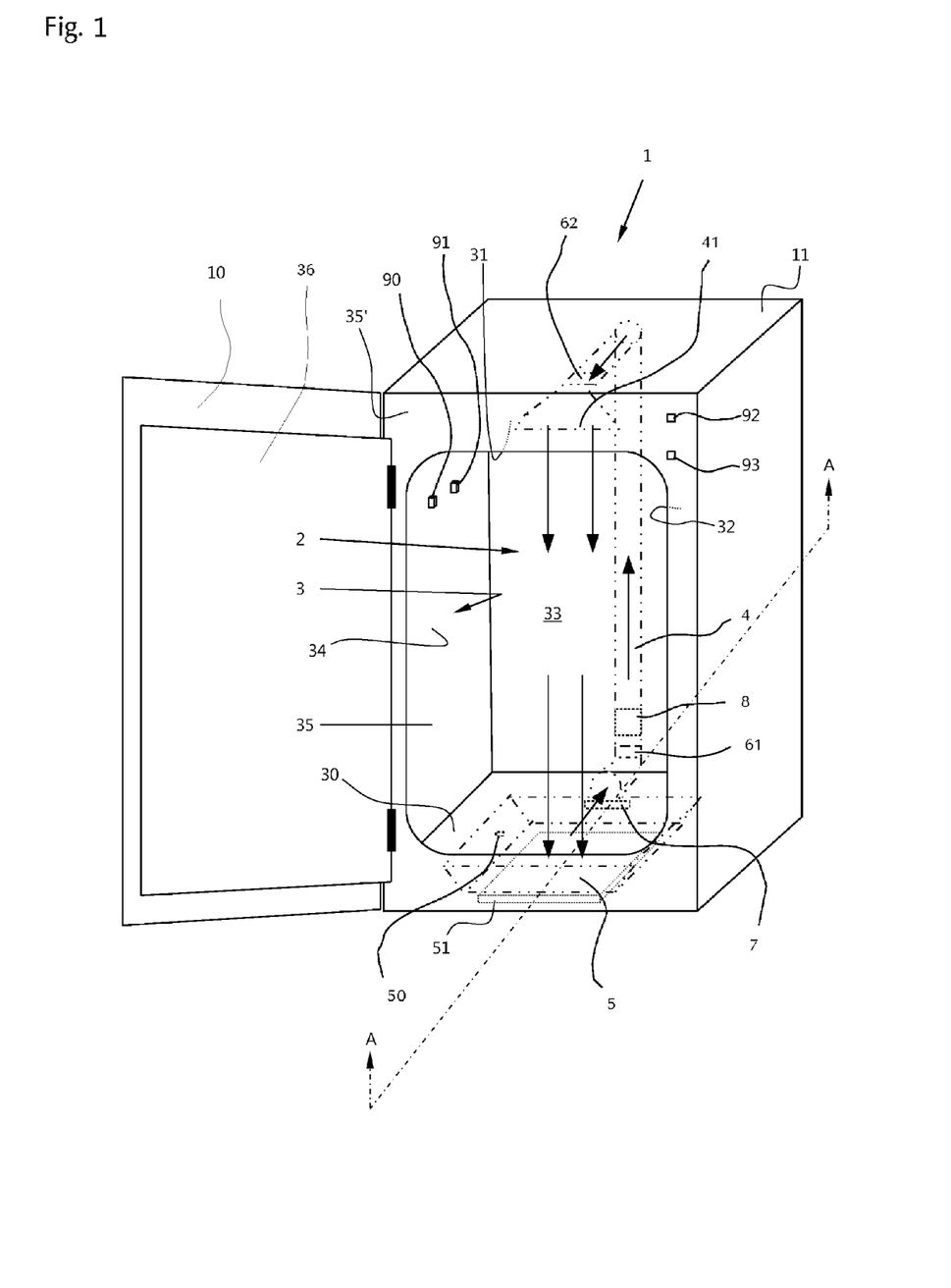
FIG. 1 is a front view of the front side of the laboratory incubator according to the present invention.

FIG. 1 shows a laboratory incubator 1 according to the present invention, in this case, by example of a gassing incubator, in a front view of the front side. The laboratory incubator comprises an outer housing 11 containing an outer door 10, enabling access to an internal chamber 2. The internal chamber 2 is enclosed by an inner housing 3 consisting of a floor 30, side wall panels 32, 33, and 34, and a ceiling panel 31. The lateral surface panel 35 facing the operator is open except for a front bezel 35' and provides access to the internal chamber 2. The lateral surface panel 35 may be closed by means of an additional, inner door 36 made of glass, for example. In the situation illustrated, both doors 10 and 36 are shown as being open.

The internal chamber 2 serves to store samples, for example, microbiological samples, that may be stored on trays mounted inside the internal chamber. For reasons of clarity, however, samples and trays are not shown. For the purpose of storing samples, a defined atmosphere is maintained within the internal chamber 2 at a predefined temperature, for example, 37° C., and predefined humidity, preferably a relative humidity of at least 80% or, more preferably, at least 90%. To protect the samples from damaging influences, it is necessary to maintain these conditions at a highly constant level and to ensure that they can be restored as quickly as possible following disruption caused, for example, by opening the doors 10 and 36.

For the purpose of humidifying the internal atmosphere, a water reservoir 5 is disposed inside the incubator and is kept filled with water during operation of the incubator 1. The water present in the water reservoir 5 may be heated by means of a heating device 51 mounted on the floor of the trough-shaped water reservoir 5. For the purpose of controlling the temperature within the internal chamber 2, a wall heating device 37 is mounted (cf. FIG. 2) for heating of side wall panels 32, 33, and 34. In the example shown, the wall heating device 37 and the heating device 51 for water reservoir 5 may operate independently of each other.

Figure 2:
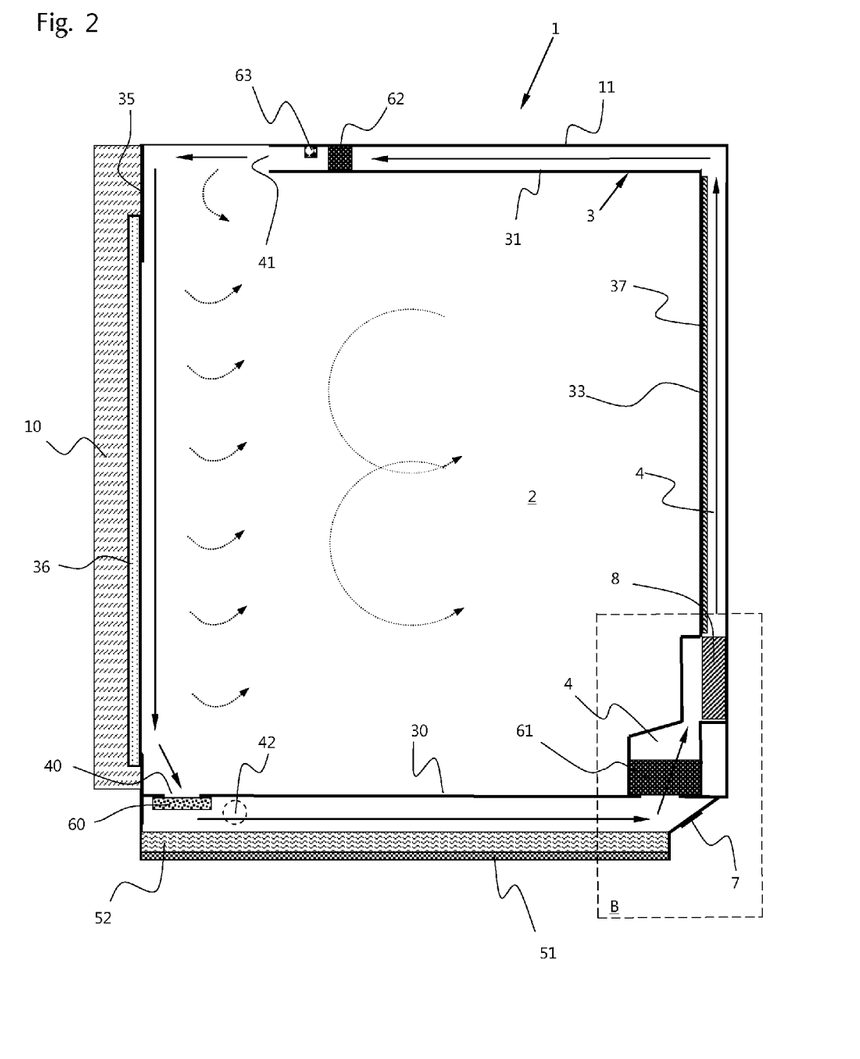
FIG. 2 is a cross-sectional view taken along the line A-A shown in FIG. 1 in a slightly modified embodiment.

As can be seen in FIGS. 1 and 2, the water reservoir 5 is mounted inside the incubator according to the present invention remotely from the internal chamber 2, in other words, below a floor panel 30. The floor panel 30 consists of a surface closed toward the internal chamber 2 except for an air inlet opening, in FIG. 1 concealed by the front bezel 35'. Air is circulated through the incubator for the purpose of transferring moisture from the water reservoir 5 to the internal chamber 2. Air enters a flow channel 4 through an air inlet opening 40 (see, FIG. 2) in the floor panel 30 adjacent to the front opening in the inner housing and the lateral surface panel 35, which flow channel 4 extends underneath the floor panel 30 from the lateral surface panel 35 to the rear side wall panel 33, then behind this panel and upwardly toward the ceiling panel 31, along the ceiling panel toward lateral surface panel 35, and ending in an air outlet opening 41. Air circulated in the flow channel by means of a fan 8 mounted behind the rear panel 33 of the inner housing 3 may flow into the internal chamber 2 via the air outlet opening 41, shown in FIG. 1 as being of a slot nozzle type.

In the embodiment shown in FIG. 1, the slot nozzle type air outlet opening is disposed closely adjacent to, and parallel to, the lateral surface panel 35, causing air to flow out of the air outlet opening directly downwardly along the lateral surface panel 35. FIG. 2 shows a slightly modified arrangement of the air outlet opening 41. The flow channel 4 ends here at the ceiling panel 31, set at a distance from the adjacent lateral surface panel 35. The air initially flows for a short distance directly along the ceiling panel 31, changing direction at the lateral surface panel 35 toward the floor panel 30, then flowing along the lateral surface panel 35 or, more particularly, along the inner door 36 that closes this panel during the operational mode, in the outer peripheral region of internal chamber 2 downwardly toward the air inlet opening 40, at which point the air is re-introduced into the flow channel 4. In all, in the embodiments shown in FIGS. 1 and 2, air thus flows barrel-like along the edge of the internal chamber 2 around the center of the internal chamber, as can be seen, in particular, in FIG. 2. The air flow is designated in FIGS. 1 and 2 by solid arrows. This barrel-like flow control around the center of the internal chamber has the advantage that samples stored at the center of the internal chamber are not immediately affected by the circulating air. Such samples are thereby exposed to a lower risk of becoming desiccated than is the case in incubators according to the prior art, where air flows mostly upwardly or downwardly across the entire internal chamber and, thus, has an immediate effect on the samples. However, in an incubator according to one embodiment of the present invention, an air exchange occurs with the center of the internal chamber only via a secondary flow caused by turbulences occurring at the edge of the main flow. This is illustrated in FIG. 2 by curved and dashed arrows. Since the secondary flow is significantly slower than the main flow, there is a lower risk of samples becoming desiccated as would be the case if they were exposed to the main flow.

Figure 3:
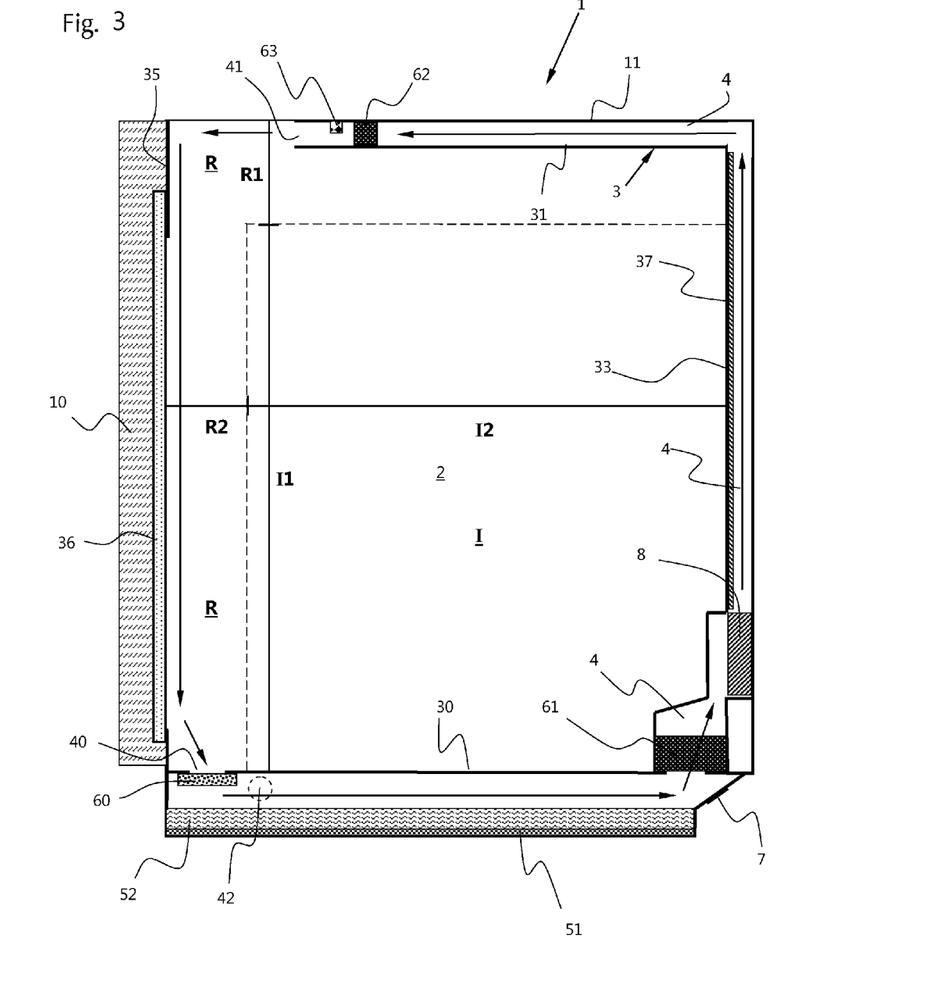
FIG. 3 is a simplified view of FIG. 2 to illustrate internal flow control.

The peripheral region of the internal chamber, where the flow control occurs, is sketched out in FIG. 3. This figure illustrates the regions of the internal chamber which are immediately supplied with air in relation to the regions of the internal chamber which are not immediately affected by air flow. The region receiving air directly from the air outlet opening is the peripheral region, identified by R in the left-hand part of the figure, adjacent to the lateral surface panel 35 and ceiling panel 31, which is itself adjacent to the top of the lateral surface panel 35. The region not immediately affected by air escaping from the air outlet opening 41 is identified by I. The width (R1 or R2) of the peripheral region R plus the width (I1 or I2) of the internal chamber region adjacent to the peripheral region is equal to the overall width of the internal chamber between the side wall panel 33 and the lateral surface panel 35 or, more particularly, between the ceiling panel 31 and the floor panel 30. The width of the peripheral region receiving air from the flow channel 4 is at most 20% of the overall width of the internal chamber—in other words, in this case, $R1/(R1+I1) \leq 0.2$ or $R2/(R2+I2) \leq 0.2$. No air is immediately taken in from the flow channel in the remainder of the internal chamber region I, where air exchange takes place due to the secondary flow derived from the main flow.

For the purpose of limiting the air supply from the air outlet opening 41 to the peripheral region R, flow control is appropriately effected parallel, or substantially parallel, to the side wall panel or lateral surface panel along which air is conducted. In this case, "substantially parallel" means that the angle of air flow in relation to the side wall panel/lateral surface panel along which air flow takes place is not more than 5°, in particular, not more than 2°. In the case shown, air is blown into the internal chamber parallel to the ceiling panel, in other words, at an angle of 0°.

Air moisture is conveyed into the internal chamber 2 by causing the air flowing through the flow channel 4 to be guided across the water reservoir 5, following entry thereof via the air inlet opening 40. As illustrated in FIGS. 1 and 2, this is preferably carried out by causing the air to be guided once across substantially the entire width of the water reservoir 5, with the result that a path of sufficient length is provided for the air to accumulate water vapor. For the purpose of reducing the entrainment of pollution into the water reservoir, a filter 60, for example, in the form of a filter membrane, is disposed above the air inlet opening 40. A HEPA filter 61 is disposed at the outlet of the water reservoir 5 in the flow channel 4 for the air containing water vapor to pass through prior to being further advanced by the fan 8 through the flow channel 4 and prior to entering the internal chamber 2 via the air outlet opening 41. As a result, any germs possibly present in the water reservoir 5 are prevented from being entrained into the internal chamber with the air flow and, thus, from contaminating the samples.

Since the fan 8 used for moving air may also set pollution free, an additional filter 62 is mounted inside the flow channel 4 in front of the air outlet opening 41 for the purpose of retaining such pollution. The flow channel 4 is, therefore, a closed system as regards air flow and is protected from pollution and contamination by means of a number of filters. In this way, the water reservoir 5, separated from the internal chamber 2 by the floor panel 30 and framed by filters 60 and 61, is particularly well protected from pollution and contamination. There is neither the risk of polluted samples stored in the internal chamber 2 directly polluting the water reservoir due to the spatial separation thereof created by means of the floor panel 30, nor is there any counter risk of germs that have entered the water reservoir, for example, due to the addition of polluted water 52 thereto, reaching the samples by means of air conveyed to the internal chamber 2 through the flow channel 4 due to the fact that a HEPA filter 61 is situated downstream of the water reservoir in the flow channel 4. Not only does this provide optimum protection of the samples, but it also extends the frequency at which the water 52 present in the water reservoir 5 needs to be changed due to pollution or contamination. The amount of maintenance required is thus significantly reduced compared with conventional incubators.

A further significant advantage of the incubator according to the present invention resides in the high degree of constancy of temperature and moisture content that may be maintained inside the internal chamber 2. The spatial separation of the water reservoir 5 and the internal chamber 2 as well as the separate means of heating the water reservoir using a heating device 51 as against the temperature control of the internal chamber 2 by means of a wall heater 37 thus contribute to better and faster regulation of the temperature of the internal chamber. The latter is regulated, for example, in accordance with the measurement results obtained from the temperature sensor 90 inside the internal chamber. A further sensor 91 is disposed inside the internal chamber 2 for the purpose of measuring the moisture content in the internal chamber. In addition, sensors 92 and 93 serve the purpose of indicating when the outer door 10 or the inner door 36 is opened. The gaining of such information makes it possible to respond swiftly to system disturbances. The opening of doors 10 and 36 generally results in the temperature in the internal chamber dropping and the humidity therein falling. For the purpose of counteracting such a disturbance, it is advisable to increase the output of the wall heater 37 and, more particularly, to boost that of the heating device 51 and, thus, raise the water temperature in the water reservoir 5 for the purpose of compensating for humidity loss in the internal chamber as swiftly as possible, thus preventing desiccation of the samples. Since, according to the present invention, in one embodiment the heating device 51 operates independently of the wall heater 37, it is possible to increase the output of the heating device 51 over and above that of the wall heater 37, such that a loss of humidity may be balanced out significantly faster than when the same heater is used for both purposes. To this end, the water temperature in the water reservoir 5 is measured by means of a temperature sensor 50, in this case, disposed in a side wall region of the water reservoir. In a preferred embodiment, the temperature sensor 50 is in a position corresponding to the minimum required water level in the water reservoir 5. The temperature sensor 50 may thus also be used as a water level gauge since, in the event of the water sinking below the desired minimum water level, the temperature sensor 50 will also become dry. Such event is reflected by an abrupt change in the temperature measured by the temperature sensor. In the event of an evaluation and control unit (not shown) detecting such an abrupt temperature change via the sensor 50, a warning is issued to signal the low water level and, if necessary, provision is made for automatic replenishment of water 52 by means of a filling device.

If, following such a disturbance and the increased heating output of the heating device 51 caused thereby, the cause of the disturbance is rectified by closing the doors 36 and 10, the temperature and humidity levels in the internal chamber rise very rapidly to the desired setpoint values. Due to the relatively intense heating of the water reservoir 5, there is, at this point, however a risk of the required temperature and humidity values being exceeded in the internal chamber. Due to the separate controllability of the wall heater 37 and the heating device 51 for the water reservoir, however, a significantly faster and more specific reaction to abrupt increases in temperature can take place than would have been possible if the two heating devices had been interconnected. The same applies to the regulation of the humidity in the internal chamber. For the purpose of precisely maintaining the latter and adjusting it as quickly as possible to the setpoint value, provision is made, according to the present invention, for the special arrangement of a cold spot 7 as an additional measure. The cold spot 7 is a region of reduced temperature allowing for condensation of excess moisture. According to the present invention, this cold spot 7, previously disposed inside the internal chamber 2 and usually at a lower region of one of the side walls, has now been removed, like the water reservoir 5, from within the internal chamber to an area below the floor panel 30. More particularly, the cold spot 7 is situated downstream of the water reservoir and connected to the end region of the latter. As particularly visible in FIG. 4, the cold spot 7 is disposed at an extended end portion of the water reservoir 5. Such an end portion is situated above the water level in the water reservoir 5 and is in the form of a downwardly sloping ramp area or extended peripheral section of the water reservoir. Moisture condensing near the cold spot 7 may thus flow back into the water reservoir 5.

Figure 4:
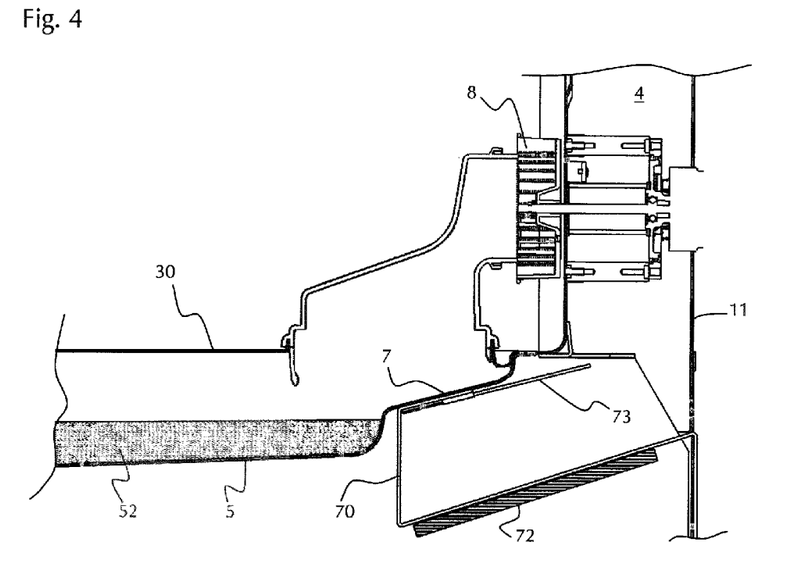
FIG. 4 is an enlarged detail of area B shown in FIG. 2 in a slightly modified embodiment of the incubator.

The temperature of the cold spot 7 is, in the present example, specifically adjustable. For this purpose, firstly, a temperature bridge in the form of an aluminum strip 70 is provided so as to be in contact with the cold spot 7 in a heat conducting manner. The application of a heat conductive paste, for example, may provide good heat-conductivity in the area of contact between the cold spot 7 and the aluminum strip 70. The aluminum strip 70 is bent in such a way that the end which is not in contact with the cold spot 7 is caused to be in contact with the outer surface of the outer housing 11. The aluminum strip 70 thus serves as a thermal bridge adapted to convey the lower outer temperature of the environment of the incubator to the cold spot 7. Secondly, in addition to such a passive thermal bridge, there is connected an active temperature control device 72 to the aluminum strip 70. Such a temperature control device may, for example, consist of an electric cooling and heating device, making it possible for the cold spot 7 to be specifically set to a predefined temperature. This not only enables the cold spot to be cooled down when excess moisture must be condensed out of the air circulating through the flow channel 4, but it also makes it possible to specifically raise the cold spot temperature for certain applications, in order, in particular, to prevent condensation from occurring. To make it possible to regulate the temperature of the cold spot 7 in accordance with a required application, a temperature sensor 73 for measuring of the cold spot temperature is also caused to be in contact with the aluminum strip 70.

The registration of the measurement results obtained from the various sensors as described above, the analysis of such measurement results, and the control of individual heating devices and of the fan output, etc., on the basis of such analysis, are carried out by means of a conventional evaluation and control device in a manner known per se. This makes it possible to effect rapid and precise control of the temperature and humidity in the internal chamber of the incubator in accordance with the relevant temperature, humidity and other measured values and, thus, in combination with the special flow control inside the internal chamber 2 of the incubator, guarantees the existence of an atmosphere in the internal chamber that is precisely adapted as required and in relation to the samples being stored.

In addition, the atmosphere in the internal chamber may not only consist of humidified air but may also contain additional gases such as nitrogen or carbon dioxide. The supply of such additional gases may principally take place in any usual manner known in the art. However, it is preferred, within the scope of the present invention, to also feed such additional gases into the flow channel 4 and not directly into the internal chamber 2, in other words, in the latter case there is a danger of desiccation of the samples due to the commercially available gases generally being dried gases having very low humidity levels. It is, therefore, preferred to feed such additional gases into the flow channel 4 in such a way that they are initially directed across the water reservoir 5, where they accumulate moisture before being fed into the internal chamber 2 via the air outlet opening 41. For this purpose, a further inlet opening 42 may be present, for example, adjacent to the air inlet opening 40 for air circulating inside the internal chamber, which inlet opening 42 serves for the introduction of gases such as nitrogen or carbon dioxide. Such gas then blends with the air in the flow channel 4, accumulates moisture in the manner described above while travelling across the water reservoir 5, passes the HEPA filter 61, then the fan 8, and, subsequently, passes through the remainder of the flow channel 4 and the filter 62 via the air outlet opening 41 into the internal chamber 2.

For the purpose of guaranteeing an optimally consistent flow of air or of the air/gas mixture in the internal chamber during the entire period of application, flow resistance meters may be allocated to the various filters 60, 61, and 62 to make it possible to detect the extent to which the filters are choked by pollution and, thus, show increasing resistance to air flow. In the case illustrated here, such a flow resistance meter 63 is allocated to the filter 62 near the air outlet opening 41. The higher the level of pollution in the filter 63, the greater the increase in flow resistance of this filter and, accordingly, in the measurement results obtained from the sensor 63. As a consequence of such an increase in the measured values, the device control means can increase the output of the fan 8. The rate of flow of the conveyed air can, thus, be maintained at a constant level.

Figure 5:
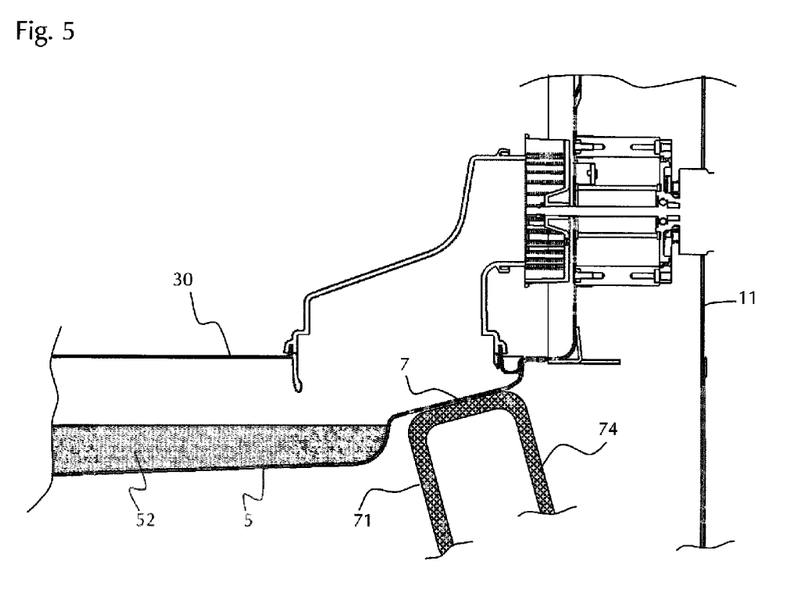
FIG. 5 is a further enlarged detail of area B shown in FIG. 2 in a further modified variant.

FIG. 5 diagrammatically shows an alternative way of achieving temperature control of the cold spot 7. Instead of the aluminum strip shown in FIG. 4, a hollow member 71 in the form of a hose system is provided. The hose system forms a conveyer circuit for the purpose of conveying a heat bearing fluid 74, for example, water. The fluid temperature may be adjusted as desired by means of a heating/cooling device inside a reservoir (not shown) included in the circuit. In a simplified version, a section of the conveyer circuit may simply be relocated to a cooler environment, for example, the exterior of the incubator, for the purpose of cooling. If cooling of the cold spot 7 is not required—for example, when normal incubation operation is not taking place, such as during a disinfection process—the fluid is drained from the hollow member 71. Heat dissipation from the cold spot 7 therefore ceases with the result that the cold spot temperature equalizes with the temperature of its environment. When cooling of the cold spot again becomes necessary, the hollow member 71 is again filled with fluid.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The present invention in its broader aspects is therefore not limited to the specific details and illustrative examples shown and described. Accordingly, departures may be made from such details without departing from the spirit or scope of Applicants invention.

What is claimed is:

1. A laboratory incubator, comprising:
an outer housing incorporating a door, and
an inner housing surrounding an internal chamber, which inner housing comprises a floor, a ceiling, three side walls and a lateral surface that can be closed by said door, said laboratory incubator further comprising a flow channel that comprises at least one air inlet opening in an end region and at least one air outlet opening in a different end region disposed in a peripheral region of said ceiling and/or in a peripheral region of at least one of said side walls adjacent to said ceiling, wherein said at least one air outlet opening is formed such that an effluent air flow is guided in a downward direction substantially parallel to at least one of the side walls and/or the lateral surface along which the effluent air flow is conducted and only in a peripheral region of said internal chamber, and wherein a water reservoir capable of being heated is disposed within said flow channel such that air flowing in the flow channel is passed across or through said water reservoir.

2. The laboratory incubator according to claim 1, wherein said flow channel is disposed between said outer housing and said inner housing.

3. The laboratory incubator according to claim 1, wherein said at least one air inlet opening is present in an outer peripheral region of said floor and preferably below the at least one air outlet opening.

4. The laboratory incubator according to claim 1, wherein the at least one air outlet opening is present in the peripheral region of said ceiling above said door and the at least one air inlet opening is disposed in a region adjacent to the bottom edge of said door, such that the air flow is guided downwardly along said door.

5. The laboratory incubator according to claim 1, wherein the at least one air outlet opening is in the form of a slot nozzle.

6. The laboratory incubator according to claim 1, wherein said water reservoir is disposed beneath said floor in the form of an upwardly open water trough.

7. The laboratory incubator according to claim 1, wherein a temperature sensor for measuring the water temperature in said water reservoir is provided in the water reservoir.

8. The laboratory incubator according to claim 7, wherein a heating device, which is separate from a heating device provided for said internal chamber, is provided for said water reservoir, which heating device is controllable according to measurement results obtained from said temperature sensor.

9. The laboratory incubator according to claim 8, wherein, in the flow channel, a filter is disposed prior to and/or following the water reservoir, which filter is selected from an air-permeable membrane, a HEPA filter or an ULPA filter.

10. The laboratory incubator according to claim 9, wherein a cold spot is provided in said flow channel in the direction of flow following said water reservoir.

11. The laboratory incubator according to claim 10, wherein, for the purpose of adjusting the temperature of said cold spot, a temperature control device is provided that is selected from the group consisting of:
a temperature bridge that is in heat-conducting contact with said outer housing and is in the form of a metal strip,
a hollow member filled with a cooling fluid and capable of being emptied,
a temperature control device for effecting active temperature control, selected from an electrical cooling device and/or heating device and a fan.

12. The laboratory incubator according to claim 11, wherein a temperature sensor is provided for the purpose of measuring the temperature of said cold spot and the temperature control device is preferably controllable depending on the measurement results of said cold spot temperature sensor.

13. The laboratory incubator according to claim 12, which comprises at least one of the following sensors:
- a sensor for ascertaining the temperature in the internal chamber (2),
- a sensor for ascertaining the moisture in the internal chamber (2),
- a sensor for ascertaining whether the door is open or closed,
- a sensor for ascertaining whether the inner door is open or closed,
- wherein said heating device for said water reservoir and/or said temperature control device for said cold spot is capable of being controlled according to measurement results of at least one of said sensors.

14. The laboratory incubator according to claim 1, wherein in said flow channel there is disposed, a fan.

15. The laboratory incubator according to claim 14, wherein a filter, a HEPA filter or an ULPA filter is disposed between said fan and said at least one air outlet opening.

16. The laboratory incubator according to claim 15, wherein a flow resistance meter is allocated to the filter and the output of the fan is adjustable according to the measurement results of said flow resistance meter.

17. The laboratory incubator according to claim 1, comprising:
- a device for the introduction of gas into the internal chamber, wherein said gas can be introduced into said flow channel.

18. The laboratory incubator according to claim 1, wherein said laboratory incubator comprises a gassing incubator.

19. The laboratory incubator according to claim 1, wherein said inner housing can be closed by an inner door in addition to said door.

20. The laboratory incubator according to claim 1, wherein the at least one air outlet opening is present in the peripheral region of said ceiling above said inner door and the at least one air inlet opening is disposed in a region adjacent to the bottom edge of said inner door, such that the air flow is guided downwardly along said inner door.

21. The laboratory incubator according to claim 7, wherein said temperature sensor is provided at the level of the minimum water level.

22. The laboratory incubator according to claim 11, wherein said metal strip comprises an aluminum strip.

23. The laboratory incubator according to claim 14, wherein said fan is disposed downstream of said water reservoir.

24. The laboratory incubator according to claim 14, wherein said fan comprises a radial fan.

25. The laboratory incubator according to claim 15, wherein said filter, said HEPA filter or said ULPA filter is disposed at the end of said flow channel.

26. The laboratory incubator according to claim 17, wherein said gas can be introduced into said flow channel upstream of said water reservoir.

* * * * *

UNITED STATES PATENT AND TRADEMARK OFFICE
CERTIFICATE OF CORRECTION

| | |
|---|---|
| PATENT NO. | : 9,902,930 B2 |
| APPLICATION NO. | : 14/454419 |
| DATED | : February 27, 2018 |
| INVENTOR(S) | : Pieczarek et al. |

Page 1 of 1

It is certified that error appears in the above-identified patent and that said Letters Patent is hereby corrected as shown below:

On the Title Page

Column 2, (57) Abstract, Line 2, change "incubator, more particularly, a gassing incubator, comprising" to --incubator, more particularly a gassing incubator, comprising--.

In the Specification

In Column 1, Line 27, change "serve to store samples, more particularly, biological and/or microbiological samples, in the internal chamber thereof," to --serve to store samples, more particularly biological and/or microbiological samples, in the internal chamber thereof,--.

In Column 2, Line 56, change "For example, they may be openings in the duct" to --For example, there may be openings in the duct--.

In the Claims

In Claim 13, Column 17, Lines 14-16, change "wherein said heating device for said water reservoir and/or said temperature control device for said cold spot is capable of being controlled" to --wherein said heating device for said water reservoir and/or said temperature control device for said cold spot are capable of being controlled--.

In Claim 14, Column 17, Line 19, change "wherein in said flow channel there is disposed, a fan." to --wherein in said flow channel there is disposed a fan.--.

Signed and Sealed this
Twenty-ninth Day of May, 2018

Andrei Iancu
*Director of the United States Patent and Trademark Office*